US012584901B2

(12) United States Patent
Jensen et al.

(10) Patent No.: US 12,584,901 B2
(45) Date of Patent: Mar. 24, 2026

(54) ELECTRONIC SINGLE USE CHEMICAL DIAGNOSTICS DEVICE

(71) Applicant: Gate Scientific, Inc., Milpitas, CA (US)

(72) Inventors: Morten Juel Jensen, Saratoga, CA (US); Kristian Michael Scaboo, Castro Valley, CA (US)

(73) Assignee: Gate Scientific, Inc., Milpitas, CA (US)

( * ) Notice: Subject to any disclaimer, the term of this patent is extended or adjusted under 35 U.S.C. 154(b) by 524 days.

(21) Appl. No.: 16/248,631

(22) Filed: Jan. 15, 2019

(65) Prior Publication Data

US 2019/0170727 A1    Jun. 6, 2019

Related U.S. Application Data

(63) Continuation of application No. PCT/US2017/042436, filed on Jul. 17, 2017.

(60) Provisional application No. 62/362,745, filed on Jul. 15, 2016.

(51) Int. Cl.
| | |
|---|---|
| *G01N 33/487* | (2006.01) |
| *B01L 3/00* | (2006.01) |
| *G01K 1/14* | (2021.01) |
| *G01K 13/00* | (2021.01) |

(52) U.S. Cl.
CPC .......... *G01N 33/48792* (2013.01); *B01L 3/52* (2013.01); *G01K 1/14* (2013.01); *G01K 13/00* (2013.01); *G01N 33/48707* (2013.01); *B01L 2200/10* (2013.01); *B01L 2200/16* (2013.01); *B01L 2300/0663* (2013.01); *G01K 2215/00* (2013.01)

(58) Field of Classification Search
None
See application file for complete search history.

(56) References Cited

U.S. PATENT DOCUMENTS

| | | | | |
|---|---|---|---|---|
| 4,826,762 A | * | 5/1989 | Klibanov | ............... G01K 11/06 |
| | | | | 374/E11.006 |
| 5,567,595 A | | 10/1996 | Kok | |
| 5,960,160 A | | 9/1999 | Clark et al. | |
| | | (Continued) | | |

FOREIGN PATENT DOCUMENTS

| | | | | | |
|---|---|---|---|---|---|
| JP | | 2006343206 A | * 12/2006 | ........ | B01L 3/502738 |
| WO | WO 1995/006240 | | 3/1995 | | |
| | | (Continued) | | | |

*Primary Examiner* — William H. Beisner
(74) *Attorney, Agent, or Firm* — Levine Bagade Han LLP

(57) ABSTRACT

An electronic diagnostics device can detect and report environmental conditions from manufacture to use. The device can include a reaction chamber configured to receive a biological sample and contain a reaction with the biological sample. A component of the biological sample can be detected based on the reaction. The device can also include one or more environmental sensors, such as a temperature sensor and a humidity sensor, to detect the environmental conditions. A processor can read data from the environmental sensors and compare the measured conditions to specified ranges. If an environmental parameter falls outside the specified range, the processor can disable the device or communicate to a user that the device should not be used to perform a diagnostic test.

42 Claims, 8 Drawing Sheets

(56)　　　　　References Cited

U.S. PATENT DOCUMENTS

| | | | |
|---|---|---|---|
| 7,638,093 B2 | 12/2009 | Wang et al. | |
| 7,659,816 B2* | 2/2010 | Wandel | B65D 55/026 |
| | | | 340/572.8 |
| 2005/0174236 A1* | 8/2005 | Brookner | G08B 13/2462 |
| | | | 340/870.01 |
| 2005/0248455 A1* | 11/2005 | Pope | G04F 10/00 |
| | | | 374/E1.004 |
| 2006/0030049 A1 | 2/2006 | Bhimani et al. | |
| 2009/0035865 A1 | 2/2009 | DeMoor et al. | |
| 2009/0041626 A1* | 2/2009 | Atkin | G01N 35/00732 |
| | | | 422/68.1 |
| 2010/0175455 A1 | 7/2010 | Dylewski et al. | |
| 2012/0173164 A1 | 7/2012 | Steuerwald et al. | |
| 2014/0210624 A1* | 7/2014 | Wandel | G08B 13/1427 |
| | | | 340/572.1 |
| 2015/0198488 A1 | 7/2015 | Nekoomaram et al. | |
| 2015/0272830 A1* | 10/2015 | Iordanov | A61J 7/0076 |
| | | | 221/1 |
| 2015/0283531 A1* | 10/2015 | Jones | B01J 19/0046 |
| | | | 506/13 |
| 2016/0107820 A1* | 4/2016 | Macvittie | B65D 83/0454 |
| | | | 221/13 |

FOREIGN PATENT DOCUMENTS

| | | |
|---|---|---|
| WO | WO 2007/132376 | 11/2007 |
| WO | WO 2018/014032 | 1/2018 |

* cited by examiner

Sample application
area

Fill
sensor
pad

Filter and detection
pads

| Photo Detector 212 | Photo Detector 212 | LED 210 | Photo Detector 212 | Photo Detector 212 |

Microcontroller 316

Battery 318

| Memory 402 | Timer 406 |
| A/D Converter 404 | Display Output 408 |

LCD Screen 120

| Temperature sensor 312 | Pressure sensor 314 | Humidity sensor 320 |

Wireless Communication circuit 410

Antenna 412

314

416     412

414

800

900

ELECTRONIC SINGLE USE CHEMICAL DIAGNOSTICS DEVICE

CROSS-REFERENCE TO RELATED APPLICATION

This application is a continuation of International Application No. PCT/US2017/042436, filed Jul. 17, 2017, which claims priority to U.S. Provisional Application No. 62/362, 745, filed Jul. 15, 2016, both of which are incorporated by reference herein in their entireties.

BACKGROUND

(1) Field of the Invention

This disclosure relates to diagnostic testing devices, and in particular to monitoring environmental conditions of diagnostic testing devices from manufacture to use.

(2) Description of the Related Art

Many diagnostic tests are today carried out in specialized laboratories. A subject will go to a clinic or a hospital to give a sample of a biological fluid such as blood, urine or saliva. This sample collection is carried out by trained personnel who manage the collection in appropriate containers, mark and register it, and send it to a clinical laboratory for analysis. The result will be conveyed back to the subject after the test has been analyzed, which can take several days.

The clinical laboratories that perform these tests require staff with a high degree of training to handle the testing and tracking of the samples as well as the daily maintenance and calibration of the diagnostic instruments according to pre-scribed standards set by the Centers for Medicare & Medicaid Services through the Clinical Laboratory Improvement Amendments (CLIA).

Having analysis done by laboratories is generally rather labor intensive when it comes to sample collection, transport, test execution and conveying the result back to the subject. Such laboratory analysis can therefore be expensive and time consuming, often delaying patient treatment.

There is therefore a need for low cost point-of-care diagnostic devices that negate the need for a centralized diagnostic laboratory. Common examples of such devices include blood glucose monitoring systems and pregnancy and ovulation test devices. These examples fall into two different categories that cover the majority of commercially available point of care consumer devices.

The first category, exemplified by the Blood Glucose Monitoring System (BGMS), involves a readout meter and separate test strips. While these types of systems have the advantage of quantification, they typically suffer from a variety of disadvantages ranging from cost and convenience to inaccurate results due to poor storage conditions of the strips and difficulty transferring the strip calibration information to the meter. Other examples of analytes measured using these types of devices include total cholesterol, tri-glycerides, HDL Cholesterol and LDL cholesterol.

The second category, exemplified by the pregnancy test devices, are self-contained, one time use test sticks. There are devices in this category that also test for influenza and cholesterol. These types of devices have the advantage of cost and convenience but typically are not quantitative, providing only a yes or no answer, or rely on a colorimetric scale that is ambiguous and difficult to interpret. There are no self-contained devices that give a quantitative, digital readout for one or more analytes.

In addition, none of the devices in either of the above categories have the ability to monitor environmental conditions during shipping and storage that may compromise the performance of the device or strip. This is especially important in devices utilizing biological molecules such as enzymes or antibodies, which even in the dry form, can degrade when exposed to humidity or high temperatures.

In order for point of care and home use diagnostic devices to achieve a high level of accuracy it is important that they are easy to use and fail safe. However, the numerous points of failure in these devices—including shipping conditions unknown to the end user—can dramatically change the accuracy and usability of the devices.

Many blood glucose monitoring systems have been developed to be able to test blood samples from a fingerstick of very small volume. This is very advantageous from an ease-of-use perspective, as it is difficult for a novice user to milk a large volume of blood from a fingerstick wound. However, in the case of a multianalyte panel such as is needed to measure a complete lipid panel, the systems in the field typically require at least 40 μL, causing difficulties in acquiring a blood sample for a novice user.

Recently there has also been a move towards electronic health monitoring at both the consumer and physician level. This trend has been enabled by the rise of powerful personal electronics such as the smartphone. There is thus a need to be able to upload and electronically track results from point of care devices.

There is thus a need in the field for an inexpensive device that is completely self-contained and disposable, has a digital readout, can measure one or more analytes from a small volume of a biological fluid, can confirm that the correct volume of sample has been applied, has the ability to monitor storage and shipping conditions and alert the user to any adverse exposures, and can communicate test results to common consumer electronics.

SUMMARY

An electronic diagnostics device can detect and report environmental conditions from manufacture to use. The device can include a reaction chamber configured to receive a biological sample and contain a reaction with the biological sample. A component of the biological sample can be detected based on the reaction. For example, the device can detect analytes in blood, urine, saliva, mucus, stool, semen, or exhaled air, or can perform molecular diagnostics such as pathogen detection, genotyping of human markers, or monitoring genetic diseases.

The device can also include one or more environmental sensors, such as a temperature sensor and a humidity sensor, to detect conditions of the environment of the diagnostics device. A processor can read data from the environmental sensors and compare the measured conditions to specified ranges.

If an environmental parameter falls outside the specified range, the processor can disable the device or communicate to a user that the device should not be used to perform a diagnostic test. The processor can disable the device or display a message if the diagnostics device is exposed for any length of time to an environmental condition outside a specified range. The processor can disable the device or display a message if the environmental condition persists for longer than a threshold period of time, or can dynamically determine a shelf life for the device based on the environmental conditions and the amount of time the device is exposed to various environmental conditions.

An electronic diagnostic device is disclosed that can have a reaction chamber, an environmental sensor, and a processor. The reaction chamber can be configured to receive a biological sample and contain a reaction with the biological sample to detect a component of the biological sample. The environmental sensor can be configured to detect environmental parameters from a time of manufacturing of the electronic diagnostic device to a time of use. The processor can be configured to read the environmental parameters from the environmental sensor and disable the electronic diagnostic device responsive to detecting an environmental parameter is outside a specified range.

A self-contained electronic diagnostic device for detecting analytes in biological fluids is disclosed. The self-contained electronic diagnostic device can have a sample inlet area, a sample reaction area with one or more detectors, a readout area for display of results, a battery for providing power to the system, a microcontroller for processing the data; and a temperature sensor for measuring temperature from time of manufacturing until time of use. The device can be rendered unusable if temperature limits are exceeded.

The temperature sensor can measure temperature only at certain intervals, for example, to save power.

The device can be shipped in a vacuum package. A built-in vacuum sensor or pressure switch in the device can detect that the package is intact until use and can render the device unusable if the package has been opened too long before use. The pressure sensor or pressure switch can measure pressure only at certain intervals, for example, to save power. The vacuum sensor or pressure switch can be used to detect the opening of the packaging, for example, activating the measurement process in the device.

The device can have a built-in humidity sensor that can verify that the device has not been exposed to excessive humidity until the time of use. The device can be rendered unusable if the humidity limit has been exceeded. The humidity sensor can measure humidity only at certain intervals, for example, to save power.

The device can have an element for tracking time (e.g., an electronic clock, for example onboard a processor or circuit board) from the point of manufacturing until the point of use. The device can be rendered unusable if a maximum allowable time has been exceeded as measured by the element for tracking time.

The device can have memory that can store calibration factors.

The readout area can be an LCD display. The results can be stored in the device. The results can be transmitted by taking a picture of the readout area with a device containing a camera. The results can be deciphered and stored in a digital record in a database or transmitted via email. The mechanism used to take a picture of the screen can be a smartphone, tablet computer, personal computer (PC) with built in or attached camera, other separate device with built-in image capture capability, or combinations thereof.

The device can have a built-in antenna-based wireless transmitter for transmitting results to another system for storing, viewing, tracking, printing, or combinations thereof. The device can have a built-in optical or infra-red wireless transmitter for transmitting results to another system for storing, viewing, tracking, printing, or combinations thereof. The device can have an electrical connection for transmitting results to another system for storing, viewing, tracking, printing, or combinations thereof.

The device can be configured to perform one or more sample preparations before detection. At least one of the sample preparations can be or have sample filtering, lysing cells or virus or spores, or combinations thereof. The lysing can be performed by electroporation, chemical reactions, chemical reactions and temperature, mechanical action, or combinations thereof. The sample preparation can include electroporation. The electroporation can include extracting sample target assay materials.

The device can detect DNA or RNA target fragments corresponding to a genomic sequence. The detection of DNA or RNA target fragments can include amplification of the target sequence using thermocycling or predominantly isothermal nucleic acid amplification. Detection of the amplified target sequence can be measured by any of an electrochemical, surface hybridization of a nucleic acid, fluorescence, chemiluminescence, absorbance, reflectance, electrochemiluminescence process, or combinations thereof. The DNA or RNA target fragments can correspond to one or more specific infectious agents. The device can be configured to measure cholesterol, high density lipids, HDL, LDL, triglycerides, glucose, hemoglobin A1C, or combinations thereof.

The device can have sample reaction area detectors based on reflective measurement. The sample reaction area detectors can have one or more light sources and one or more light sensors. The device can have one or more detection pads. Each of the one or more reflective sensors is configured to sense the reflected light from each of one or more detection pads. The detection pads can have at least one covalently attached dye precursor and all other reagents required for detection immobilized on the pad. The device can have a stack of filter pads fluidically connecting the sample inlet port with the detection pads. The device can have a smaller initial filter pad connected directly to the sample inlet port and a larger pad connecting the initial filter pad with the detection pads. The smaller initial filter pad can reduce the sample volume requirement. The detection pads can have a stack of one or more filter pads. One, some or all of the filter pads can have chemical reagent coatings. The detection pads can be circular.

The sample reaction area detectors can be based on electrochemical measurement. For example, the sample reaction area detectors can have one or more electrochemical sensors. The device can have a sensor to detect that enough sample liquid has been applied to the device. The sample liquid detection can include detection of resistance change across two electrodes due to contact with sample liquid. The sample volume can be about 20 μl or less than about 20 μl. The sample can include blood, nasal mucus, saliva, urine, cervical mucus, stool, epithelial cells, a biopsy sample, nasopharyngeal swab, semen, pap smear, urethra swap, skin swap, expelled air, or combinations thereof.

One or more reagent fluids can be moved or released from a closed pouch by a user pushing or sliding a mechanical member. Reagent fluid can be moved or released from the closed pouch by use of a spring element and a resistive element that can be coupled to an electrical conducting element by use of meltable material, such as a meltable metal that is solid at room temperature but that melts below the destructive temperature of the other components in connection with the meltable metal. Heating the resistive element can lead to the melting of the meltable metal. A mechanical link can be broken when the meltable metal melts. The breaking of the mechanical link can cause the spring activation being engaged to move or release reagent fluid.

Multiple processing steps in the device are controlled by use of a spring elements and resistive elements that are connected to electrical conducting elements by use of meltable metal. The meltable metal can be solid at room temperature (e.g., ~70 degrees F.) but that can melt below the destructive temperature of the other components in connection with the meltable metal. The heating of the resistive element can lead to the melting of the meltable metal. Mechanical links including the meltable metal can be broken when the meltable metal melts, breaking the mechanical links. The breaking of the mechanical links can cause the springs activating several fluid movements at different time points during the reaction.

The temperature sensor can measure the temperature during time of use for adjusting the biological measurements in response to the temperature or to render the device invalid if temperature limits are exceeded.

A self-contained electronic diagnostic device for detecting analytes in biological fluids is disclosed. The device can have a sample inlet area, a sample reaction area with one or more detectors, a microcontroller for processing the data, and a temperature sensor for measuring temperature from time of manufacturing until and during time of use. The device can be rendered unusable by the microcontroller if predefined temperature limits are exceeded as measured by the temperature sensor.

The device can have an electrical connector (e.g., a power cord and/or plug). The electrical connector can deliver power to the device during processing. The device can have a battery for powering the device. The device can have solar cells for powering the device.

DETAILED DESCRIPTION

Figure 1:
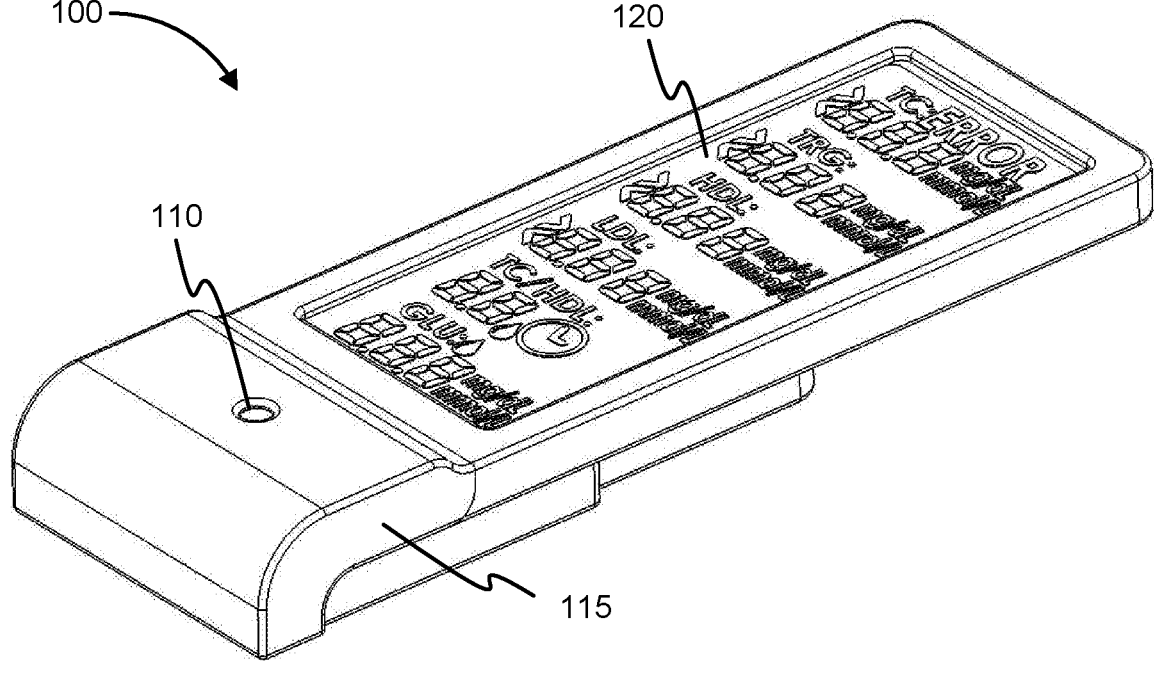
FIG. 1 illustrates one example of a single-use diagnostics device configured to detect and report environmental conditions from manufacture to use.

FIG. 1 illustrates a single-use diagnostics device 100 that can detect and report environmental conditions from manufacture to use. The device 100 can be a device usable to detect blood analytes such as cholesterol or glucose, or a device configured to perform molecular diagnostics such as pathogen detection, genotyping of human markers, or monitoring genetic diseases. The device 100 can be configured to analyze a biological sample, such as blood, urine, saliva, mucus, stool, semen, or exhaled air, or cells, proteins, or nucleic acid isolated from a biopsy sample, a nasopharyngeal swab, a pap smear, or a skin swab. The biological sample tested by the device 100 may be small, such as less than 20 µl in volume.

The device can measure a lipid panel of a patient's blood, for example in order to achieve inexpensive, multiplexed detection of different analytes from a small volume of a biological sample. The device 100 can employ predominantly vertical capillary flow to move the sample through purification and detection regions of the device 100. Upon reaching the detection regions, the analytes can be enzymatically processed to produce a color that is related to the concentration of each analyte in the sample. This color can then be detected and quantified using a reflectance measurement that converts the optical signal to an electronic signal that can be displayed to a user. The device 100 may be used in hospitals, homes, or any other location to perform a diagnostic test on a biological sample taken from a patient, without the cost and time of remote laboratory testing.

The device 100 can be packaged and shipped to consumers, where the device 100 may be used months or years after the date of manufacture. To ensure accuracy of the device 100 at the time of use, the device 100 can track the environmental conditions during shipment and storage. If the device 100 is exposed to environmental conditions outside specified ranges, the accuracy of a diagnostic test performed by the device 100 may be reduced. For example, reagents used in the device may be stable only for rated temperature and humidity ranges. Accordingly, if the device 100 detects environmental conditions outside a specified range, the device 100 may be disabled or deactivated, or may otherwise communicate to a user that the device 100 should not be used to perform a diagnostic test.

As shown in FIG. 1, the diagnostics device 100 can include a sample inlet 110, a reaction chamber 115, and a display 120. A biological sample can be applied to the sample inlet 110 and analyzed in the reaction chamber 115. Results of the analysis can be displayed on the display 120, which can be an LCD, an OLED display, an electronic ink (E Ink) display, or other type of display suitable for displaying information to a user. Additionally or alternatively, the display 120 can include one or more LED lights that can be turned on or off to convey information to the user.

Figure 2:
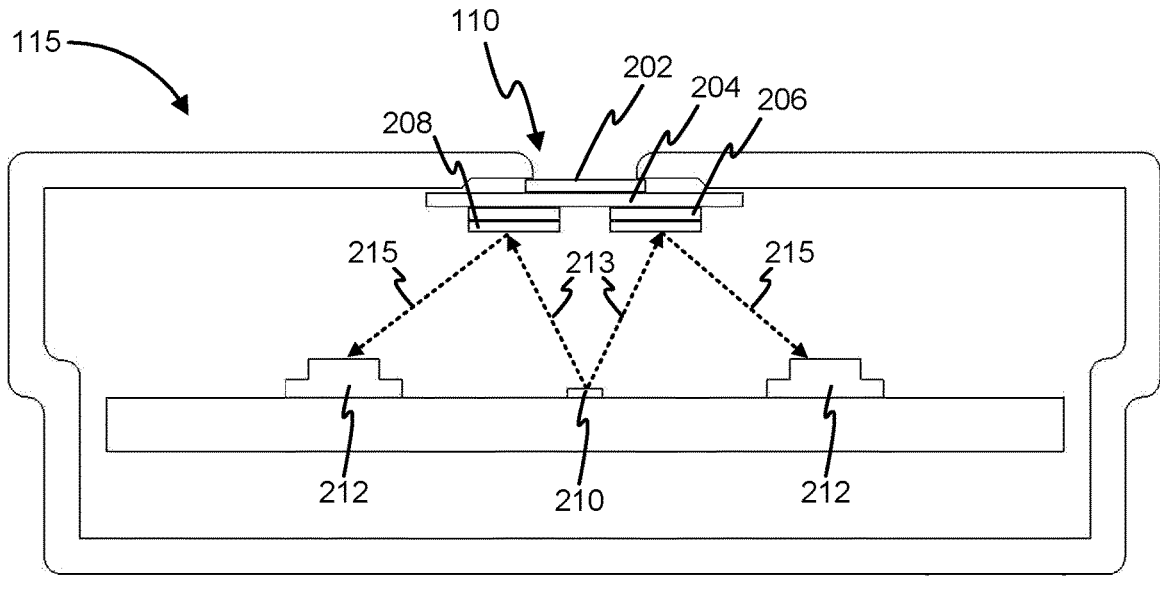
FIG. 2 illustrates a cross-section of an example reaction chamber configured to detect a blood analyte.

FIG. 2 illustrates a cross-section of a reaction chamber 115 configured to detect a blood analyte. The reaction chamber 115 may be configured similarly for performing other diagnostic functions. In the example of FIG. 2, a blood sample can be applied to the sample inlet 110, where it can contact a circular sample pre-filter 202. The pre-filter 202 can be comprised of a glass fiber filter (e.g., GF/DVA from GE Healthcare Life Sciences), and can remove interfering substances such as blood cells from the sample. The pre-filter 202 can have a slightly larger diameter than the sample inlet 110, and can have a large thickness to enable vertical filtration of the sample with low horizontal spreading. The pre-filter 202 can be treated with a surfactant or spreading solution and a saline solution to increase flow and reduce lysing of blood cells. The pre-filter 202 can additionally or alternatively be treated with an anticoagulant such as heparin to reduce blood clotting.

After passing through the pre-filter 202, the sample can contact a fine filter 204. The fine filter 204 can be an asymmetric membrane, such as the Vivid™ GF membrane by Pall Inc., and can remove any remaining blood cells in the sample without lysing the blood cells. The fine filter 204 can also be treated with a spreading solution (e.g., a wetting solution or a hydrophilic solution), saline, or an anticoagulant. The fine filter 204 can have a diameter that is larger than the diameter of the pre-filter 202, but small enough to limit horizontal spreading of the sample.

The sample can next contact one or more intermediate matrices 206, which can filter out other interfering compounds in the sample. For example, in a device 100 configured to detect HDL cholesterol, the intermediate matrix 206 can include a filter material incorporating reagents that precipitate low-density lipoproteins from the sample. Examples of such reagents include polyanions such as phosphotungstate or dextran sulfate coupled with a divalent cation salt such as $MgCl_2$. One example of a suitable filter material is Cytosep™ 1660 by Ahlstrom Inc. The intermediate matrices 206 may also be treated with a spreading compound to facilitate sample flow.

The sample can then reach one or more detection pads 208. The detection pads 208 can incorporate or be covalently bonded to reagents that, upon reacting with a desired analyte, can produce a colorimetric response. The detection pads 208 can also include reagents for stabilizing the color-producing reagents. Example membrane types that may be used for the detection pads 208 include Biodyne™ A or Biodyne™ C produced by Pall Inc. Biodyne™ C can be advantageous for covalently coupling reagents due to the carboxyl groups present that can be activated and then coupled to amine-containing moieties.

As shown in FIG. 2, the reaction chamber 115 can include an LED light source 210 and one or more optical sensors 212. The light source 210 can emit light 213 onto the detection pads 208. Light 215 reflected from the detection pads 208 can be detected by the optical sensors 212. Based on the reflected light 215 detected by the optical sensors 212, a presence or amount of a desired analyte in the sample can be determined.

Figure 3:
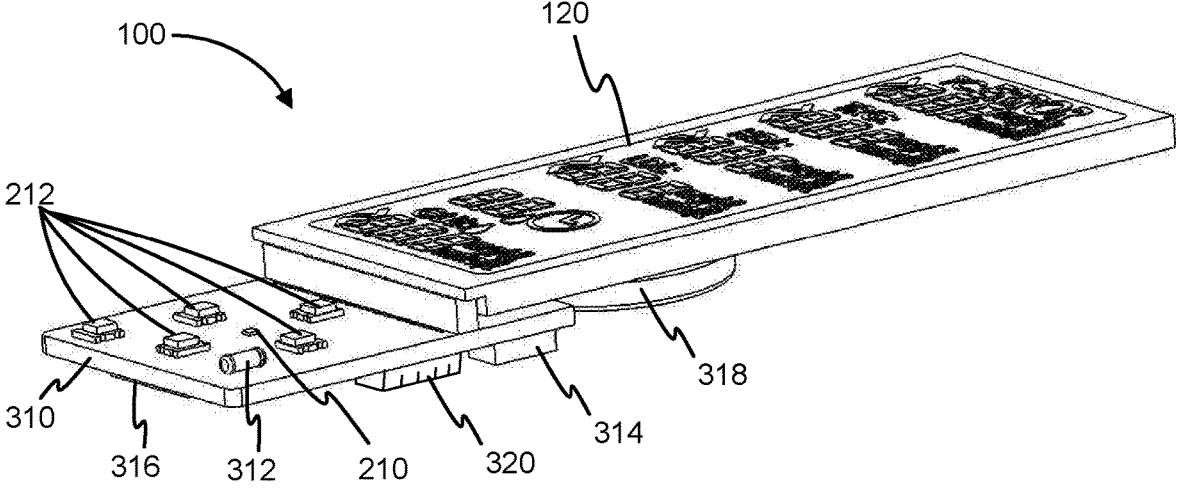
FIG. 3 illustrates example electronics of the diagnostics device.

FIG. 3 illustrates that the device 100 can include a circuit board 310 supporting the light source 210 and optical sensors 212. The circuit board 310 can include a temperature sensor 312, a pressure sensor 314, a humidity sensor 320, and a microcontroller 316. A battery 318 can be coupled to the circuit board 310 and the display 120, and the circuit board 310 can communicate with the display 120 to display information to a user.

The battery 318 provides power to the components of the circuit board 310 and the display 120. Depending on power consumption of the components, the battery 318 can be a lithium coin cell, such as CR2032, or two AAA batteries for higher power devices. The battery 318 can supply, for example, approximately 3 volts for operating the device 100.

The temperature sensor 312 can be a diode-based temperature sensor, a thermistor, or another type of sensor configured to measure temperature of the device 100. The temperature sensor can be calibrated during manufacture of the device 100 and can have an accuracy of approximately +/−2° C.

The pressure sensor 314 can detect a pressure of an environment surrounding the device 100. For example, because the device 100 may be packaged in a vacuum-sealed packaging, the pressure sensor 314 can measure the pressure in the package to determine whether the package is still sealed. A pressure above, for example, 0.75 bar may indicate that the package has been opened. The pressure sensor 314 can be a sensor, such as an Infinion Technologies™ DPS310XTSA1 sensor, configured to output a pressure reading to the microcontroller 316. The pressure sensor 314 can be a vacuum switch or other type of device capable of measuring a pressure or detecting a pressure change.

The humidity sensor 320 can measure the humidity inside or in the environment surrounding the device 100. The humidity sensor 320 can be a capacitive humidity sensor, where changes in humidity change capacitance of the sensor. The capacitance change can be detected by an oscillator circuit, which converts the capacitance change into a frequency measurable by the microcontroller 316. The humidity sensor 320 can be a digital humidity sensor, such as Measurement Specialties™ HPP845E034R5.

The temperature sensor can be a material that permanently changes properties upon exposure to higher or lower levels of temperature and therefore only needs to be read once before use of the device, example of such material is OMEGALAQ® which changes appearance when a certain temperature is reached, the appearance change can be measured by the microcontroller 316 using an optical sensor 212 when exposed to light from LED 210. Another material may be fields metal which melts when a certain temperature is reached and whereupon the melting of the metal an electrical connection can be permanently broken which can be detected by the microcontroller 316. Yet another material may be a wax that melts upon exposure to elevated temperature and where the melting of the wax enables a contact to close or open and where the closing or opening of the contact can be detected by the microcontroller 316.

The humidity sensor can be a material that permanently changes properties upon exposure to higher levels of humidity and therefore only needs to be read once before use of the device, examples of such material is copper(II) chloride based indicator impregnated on blotting paper where a certain humidity level will permanently affect the appearance of the material, the appearance change can be measured by the microcontroller 316 using an optical sensor 212 when exposed to light from LED 210.

In another implementation, the detecting of excessive temperature and/or humidity from manufacture to use can be accomplished by having a reagent or a combination of reagents of which one or many have a sensitivity to temperature and/or humidity and where the change in the reagent can be measured by the microcontroller 316 by use of electrochemical detection or by reflective measurement or by fluorescent detection or by absorbance measurement or by conductivity measurement or by other type of detection technologies. Examples of such a reagent could be a lyophilized enzyme like glucose oxidase and dried glucose which would react with the enzyme upon wetting and where the reaction would be measured optically by microcontroller 316 and where the reaction would yield a detected value outside a programmed range if the device 100 had been exposed to excessive temperature and/or humidity.

In another implementation of the device, the powering of the device can be accomplished by an external connector to the device or by use of inductive charging or wireless energy transmitted to an antenna in the device or by solar cells. This can be in addition to or instead of the built in battery 318.

Figures 4A, 4B:
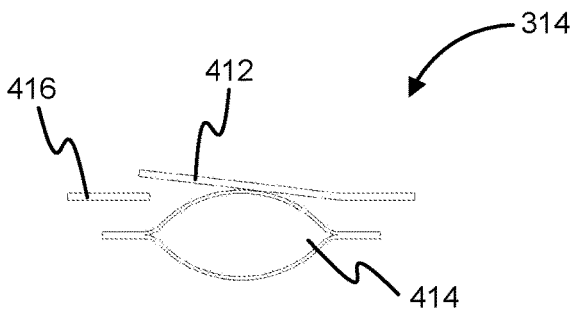
FIG. 4A is a schematic diagram of an example diagnostics device.
FIG. 4B illustrates an example vacuum switch for use as a pressure sensor.

FIG. 4A is a schematic diagram of an example device 100. As shown in FIG. 4A, the light source 210, the optical sensors 212, the battery 318, the display 120, the temperature sensor 312, the pressure sensor 314, and the humidity sensor 320 can be electronically coupled to the microcontroller 316.

The microcontroller 316 can be a low power microcontroller, such as an STMicroelectronics™ STM8L152M8T6 or similar microcontroller, which can be operated using the voltage output by the battery 318 and which can use little power in an active mode in the range of <1 mA and very little power in a standby mode in the range of <10 μA. The microcontroller 316 can periodically sample the environmental parameters of the device 100, enter an active mode to perform a diagnostic test when a biological sample is input to the device 100, and disable the device 100 if an environmental parameter falls outside an acceptable range. As shown in FIG. 4A, the microcontroller 316 can include a memory 402, an analog to digital converter 404, a timer 406, and a display output 408. The microcontroller 316 can include other circuitry in addition to or instead of these components, such as circuitry for communicating with other sensors or external devices. For example, the microcontroller 316 may include a wireless communication circuit 410 and an antenna 412 for transmitting information via near field communication, RFID or Bluetooth.

The memory 402 can include a non-volatile memory storing executable instructions for measuring environmental parameters, performing a diagnostic test, and disabling the device 100 or communicating to a user if the environmental parameters fall outside acceptable ranges. The memory 402 can store calibration factors for the optical sensors 212, temperature sensor 312, pressure sensor 314, and humidity sensor 320, as well as the acceptable ranges for temperature, pressure, and humidity in the environment of the device 100. As the environmental parameters are measured or a diagnostic test is performed, corresponding data may be written to the memory 402. In addition to the non-volatile memory, the memory 402 can include a volatile memory for use during program execution.

The analog to digital converter 404 can sample and digitize analog signals received from the sensors 212, 312, 314, and 320. For example, the analog to digital converter 404 can convert an analog signal to a 12 bit digital value. The analog to digital converter can store the digital samples of the sensor data in the memory 402.

The timer 406 can generate clocks for program execution, as well as track time since the device 100 was manufactured or since an environmental parameter moved outside an acceptable range. The timer 406 may have an accuracy between approximately +/−1% to +/−12%. The timer 406 can be regulated by an external crystal resonator if increased accuracy is desired. The microcontroller 316 can measure a lifetime of the device 100 based at least in part on the timer 406. For example, the microcontroller 316 may be programmed to disable the device 100 after a specified expiration time.

The display output 408 can communicate with the display 120 to display information to a user. Information displayed by the display 120 can include diagnostic information measured by the device 100, such as the presence or absence of a target analyte or nucleic acid sequence detected in the biological sample input to the device 100, or the concentration of a target analyte measured by the device 100. The display output 408 can send environmental information for display by the display 120. For example, the display output 408 can display information indicating that at least one of the temperature, humidity, and pressure of the device 100 environment fell outside an acceptable range, and provide an amount of time the parameter was outside the acceptable range. The display output 408 can also indicate on the display 120 if the expiration time has been exceeded for the device 100. The display output 408 can illuminate an LED to indicate that the environmental parameters have fallen outside the acceptable range at any time since manufacture. The display output 408 can provide information about the environmental parameters in other manners.

One of the fluidic pads 202, 204, 206, or 208 can function as a fill sensor to detect when the sample has been applied and whether enough sample has been applied. Another implementation of a fill sensor is to use two separate electrodes where the conductivity between the electrodes can rise when the sample is applied to the device 100. This conductivity increase can be detected by the microcontroller 316 and can signal to the microcontroller that processing of sample should be initiated. The conductivity increase can also be used to bring the microcontroller 316 from a low power mode to a higher-power, active mode for processing the sample.

FIG. 4B illustrates an example vacuum switch that can be used as the pressure sensor 314. Inside the pressure sensor 314, a contact arm 412 can be held open by a sealed pouch 414. If pressure in the environment surrounding the pressure switch 314 increases above the pressure in the sealed pouch 414, the pouch 414 can deflate and allow the contact arm 412 to touch a contact area 416. The contact between the contact arm 412 and the contact area 416 can complete an electrical circuit and allow a current to flow, and the current can be detected by the microcontroller 316. A current detected by the microcontroller 316 can indicate that packaging containing the device 100 has been opened. The microcontroller 316 may enter an active state upon detecting the current, as it may be likely that the device 100 will soon be used to perform a diagnostic test. The microcontroller 316 may disable the device 100 after a fixed amount of time after detecting the current, such as eight hours, if a sample has not been added to the device 100 within that time.

Figure 5:
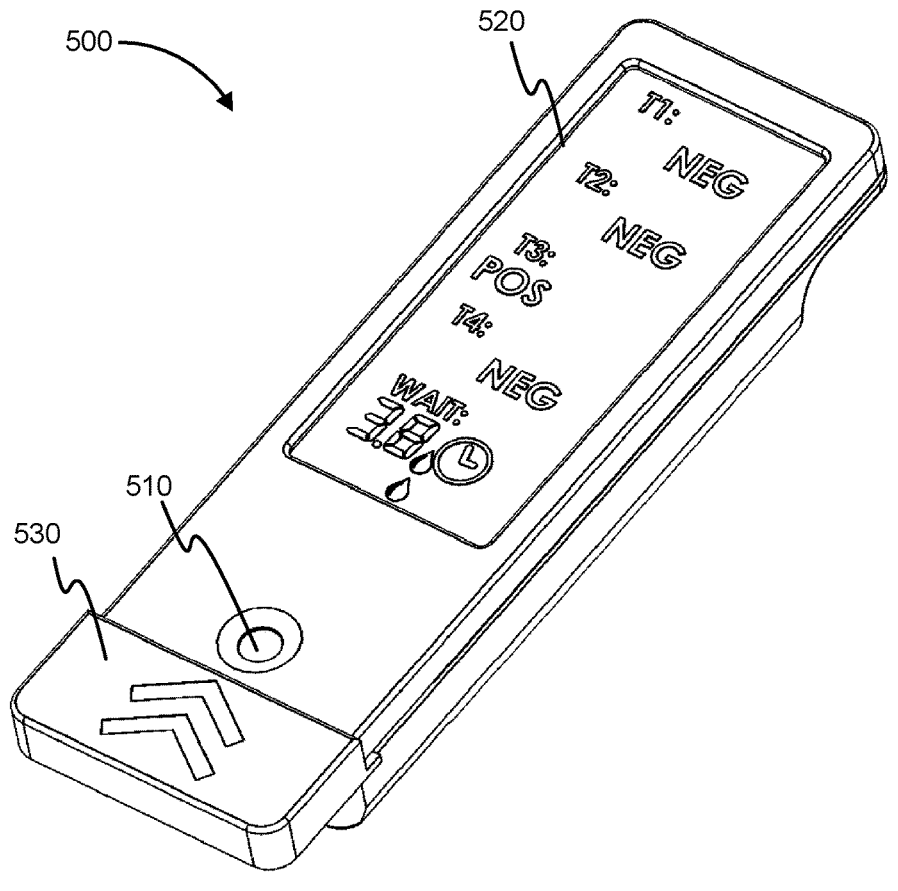
FIG. 5 illustrates another example of a single-use diagnostics device configured to detect and report environmental conditions from manufacture to use.

FIG. 5 illustrates another example single-use diagnostics device 500. The device 500 can be configured to identify the presence of a specified nucleic acid sequence in a sample. Like the device 100, the device 500 can include a sample inlet 510 and a display 520. The device 500 can further include a slidable inlet cover 530 configured to slide over the sample inlet 510. Processing of a sample deposited in the device 500 can be activated by sliding the inlet cover 530 over the sample inlet 510.

Figure 6:
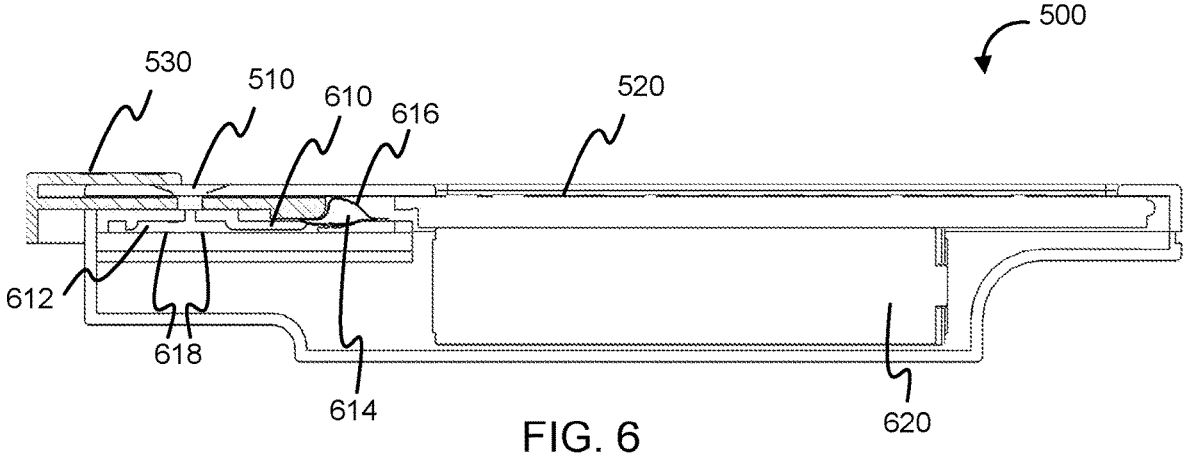
FIG. 6 illustrates a cross-section of an example diagnostics device.

FIG. 6 illustrates a cross-section of the device 500. As shown in FIG. 6, the device 500 can include a fluidic structure 610, a reaction chamber 612, and batteries 620, in addition to the sample inlet 510, the display 520, and the slidable inlet cover 530. The fluidic structure 610 can implement a dilution buffer pouch 616 that can hold a dilution buffer 614 that can mix with the sample to facilitate reactions for identifying a target nucleic acid sequence in the sample. The reaction chamber 612 can house dried reagents that can bond to target nucleic acid sequences if present in the sample. The slidable inlet cover 530 can activate piercing of the dilution buffer pouch 616 when closed over the sample inlet 510, releasing the dilution buffer 614 into the reaction chamber 612. Accordingly, after the sample is input to the sample inlet 510 and the inlet cover 530 is closed over the sample inlet 510, the dilution buffer can mix with the sample and the dried reagents in the reaction chamber 612 to initiate the reactions for identifying a target nucleic acid sequence. The detection of nucleic acid sequences can be performed using isothermal nucleic acid amplification by having a temperature controlled chamber 612 wherein electrodes 618 are located on a surface of the chamber 612. The electrodes 618 can be coated with oligonucleotide capture probes that bind to a target nucleic acid sequence. During the isothermal amplification process, an oligonucleotide indicative of target amplification can bind to the modified electrodes 618, thereby generating a signal change at the electrodes 618 that can be detected by the microcontroller 316. The temperature of the chamber 612 can be controlled by having a heated surface underneath the chamber 612.

Figure 7A:
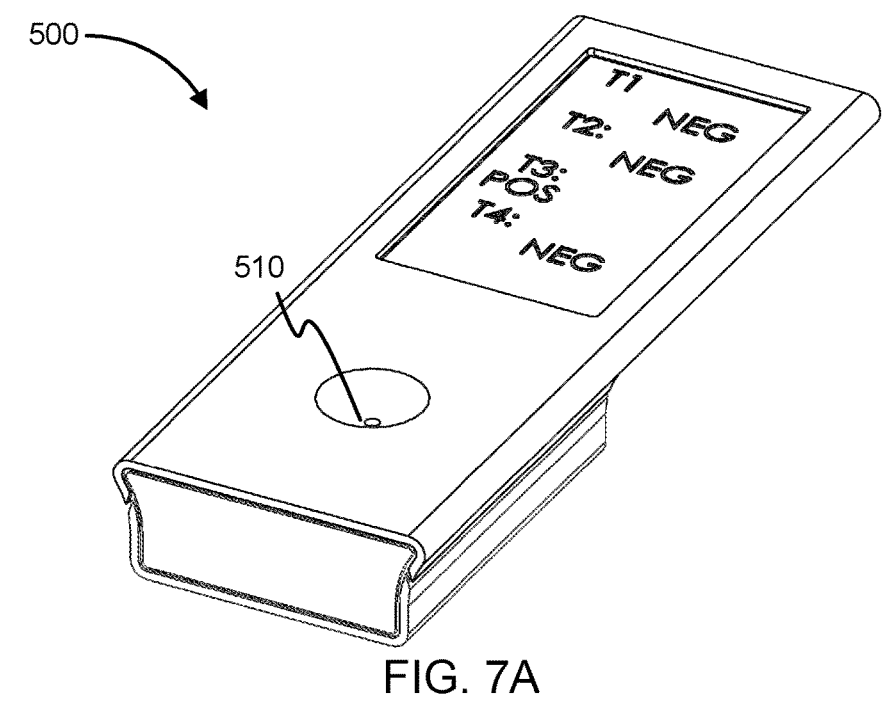
FIGS. 7A-7B illustrate example structures enabling electronic activation of the diagnostics device.
Figure 7B:
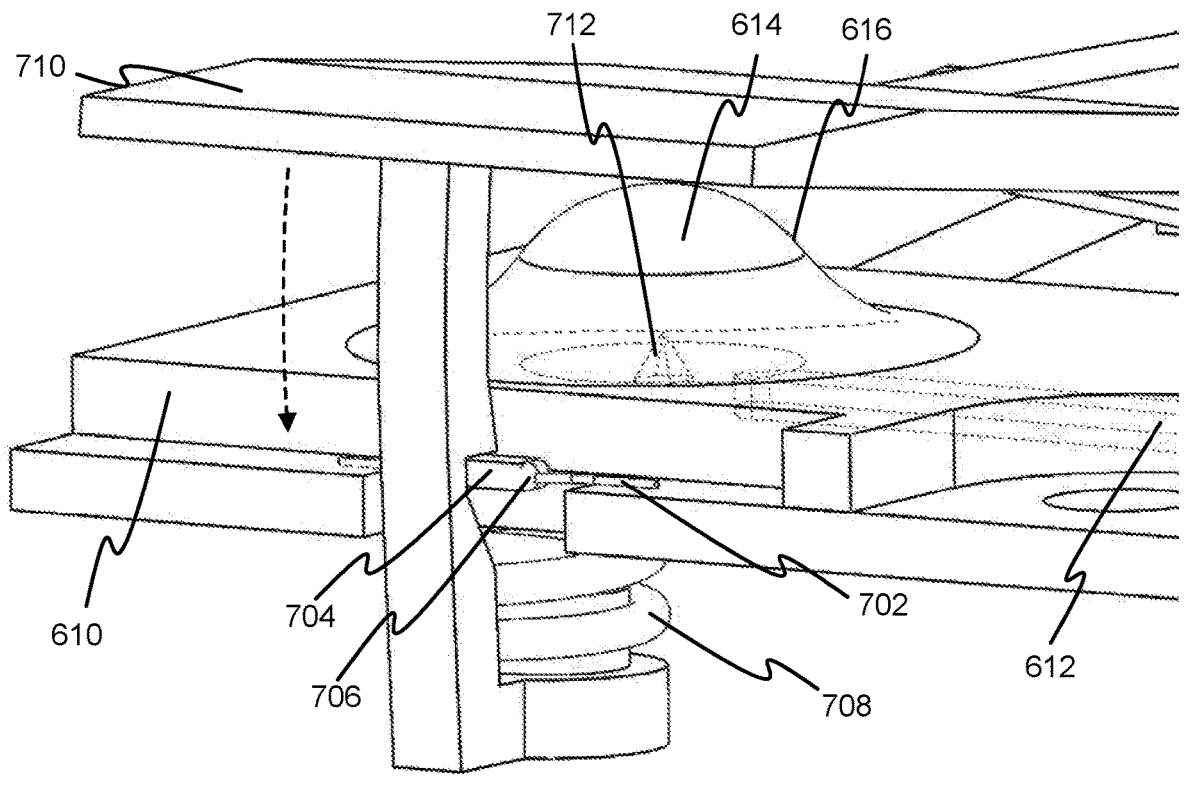

Sample processing in the device 500 can be activated electronically. FIG. 7A illustrates an example of the device 500 without the slidable inlet cover 530, in which sample processing can be activated electronically. FIG. 7B illustrates an example mechanism for the electronic activation. As shown in FIG. 7B, a wire 702 can be coupled to a spring 708 and soldered to a resistive element 704 by a low-melt temperature metal 706. The wire 702 can be directly connected to the spring 708, or can be coupled to a circuit board (not shown) that is in turn coupled to the spring 708. For example, the wire 702 can be soldered to the circuit board and the other side of the circuit board can have a spring creating a force through an arm, where the melting of the solder can release the spring force. When a user provides an input into the device 500, such as applying a sample or pressing a button, electrical current is provided to the resistive element 704. The current in the resistive element 704 generates heat, causing the metal 706 to melt. As the metal 706 melts, the resistive element 704 can disconnect from the wire 702. The disconnection of the wire 702 can release tension on the spring 708, which can pull a plate 710 down onto the fluidic structure 610. A spike 712 coupled to the bottom of the plate 610 can pierce the dilution buffer pouch 616, releasing the dilution buffer 614 into the reaction chamber 612 and initiating processing of the sample. The melting of the metal 706 and thereby breaking of the linkage of the wire 702 to the resistive element 704 can be used for other fluidic and mechanical movements in the device 100 by use of a spring 708 or no spring, such as closing of a chamber, pumping of fluid, or indicating a state to a user or preventing or enabling mechanical actions by a user. There can be one or more such activated mechanisms in a device 100 alone or along with user activated mechanisms. The compound 706 can be low melt temperature metal, such as fields metal or other metals that melts at a temperature between 25° C. and 250° C., or it can be other compounds such as polymers that melt upon exposure to heat, such as plastic or wax.

Detecting Environmental Conditions

Figure 8:
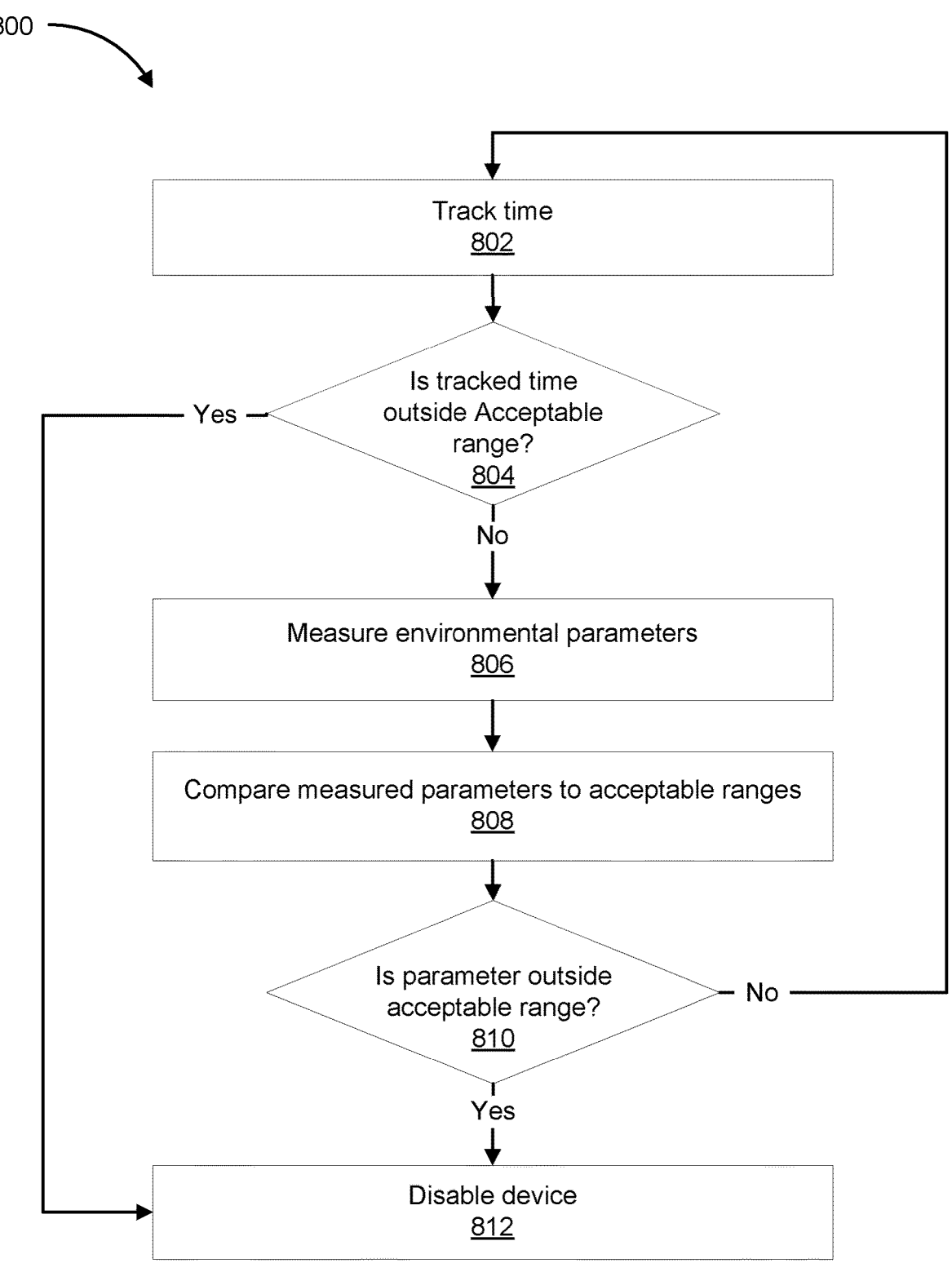
FIG. 8 is a flowchart illustrating an example process for tracking environmental conditions of a single-use diagnostics device from manufacture to use.

FIG. 8 is a flowchart illustrating an example process 800 for tracking environmental conditions of a single-use diagnostics device from manufacture to use. The process 800 is described with respect to the device 100, but may instead track the device 500 or another diagnostic device.

As shown in FIG. 8, the device 100 can track time 802 from time of manufacture and compare the time from manufacture to an expiration limit 804. If the tracked time is determined 804 to have exceeded the expiration time then the device 100 can disable 812 the device and/or communicate information to a user indicating that the device 100 should not be used.

If the expiration time has not been exceeded, the device 100 can measure 806 environmental parameters, such as temperature, humidity, and/or pressure. The device 100 can measure 806 the environmental parameters from the time of manufacture to a time of use, and optionally can store the measured parameters in a memory. To save power, the device 100 may operate in a low power mode during shipment and storage, exiting the low power mode periodically to measure 806 the environmental parameters. For example, the device 100 may sample the environmental parameters at a frequency approximately once every minute, or another frequency deemed appropriate.

The device 100 can compare 808 each sample of the environmental parameters to acceptable ranges. For temperature, the device 100 may have an acceptable temperature range defined by reagents used in the device for identifying blood analytes, target nucleic acid sequences, or other components of a biological sample. The reagents may, for example, be rated as stable from 5° C. to 30° C. At each temperature measurement, the device 100 can determine whether the measured temperature is within this range. Similarly, the reagents can define an acceptable humidity range for the device 100. For example, the reagents may be rated as stable for a relative humidity under 10%. At each humidity measurement, the device 100 can determine whether the measured humidity is within this range. Finally, the device 100 may determine whether the packaging of the device 100 has been opened by measuring the pressure of the environment. An acceptable range for pressure may be a pressure of a vacuum-sealed package, such as less than 0.75 bar. At each pressure measurement, the device 100 can determine whether the pressure is within this range. The device 100 can use the pressure measurement instead of a humidity measurement, as humidity may be relatively stable while the packaging is intact and may vary significantly if the packaging is opened.

If the device 100 determines 810 a measured environmental parameter is outside the respective acceptable range, the device 100 can disable 812 the device and/or communicate information to a user indicating that the device 100 should not be used. To disable 812 the device 100, the device may execute code to render the device 100 unusable. For example, the device 100 can execute code to enter a permanent low-power state, in which the environmental parameters are no longer measured and which cannot be exited to perform a diagnostic test. The device 100 can additionally or alternatively display a message via the display 120, or can illuminate an LED indicating to a user that the device 100 should not be used. A message can instead be conveyed to an external device, such as a display on the packaging of the device 100, a user's mobile phone, or an external reader. The device 100 may mechanically prevent use, for example by tripping a switch that, when activated, physically blocks the sample inlet 110 and prevents a user from placing a biological sample in the device.

Figure 9:
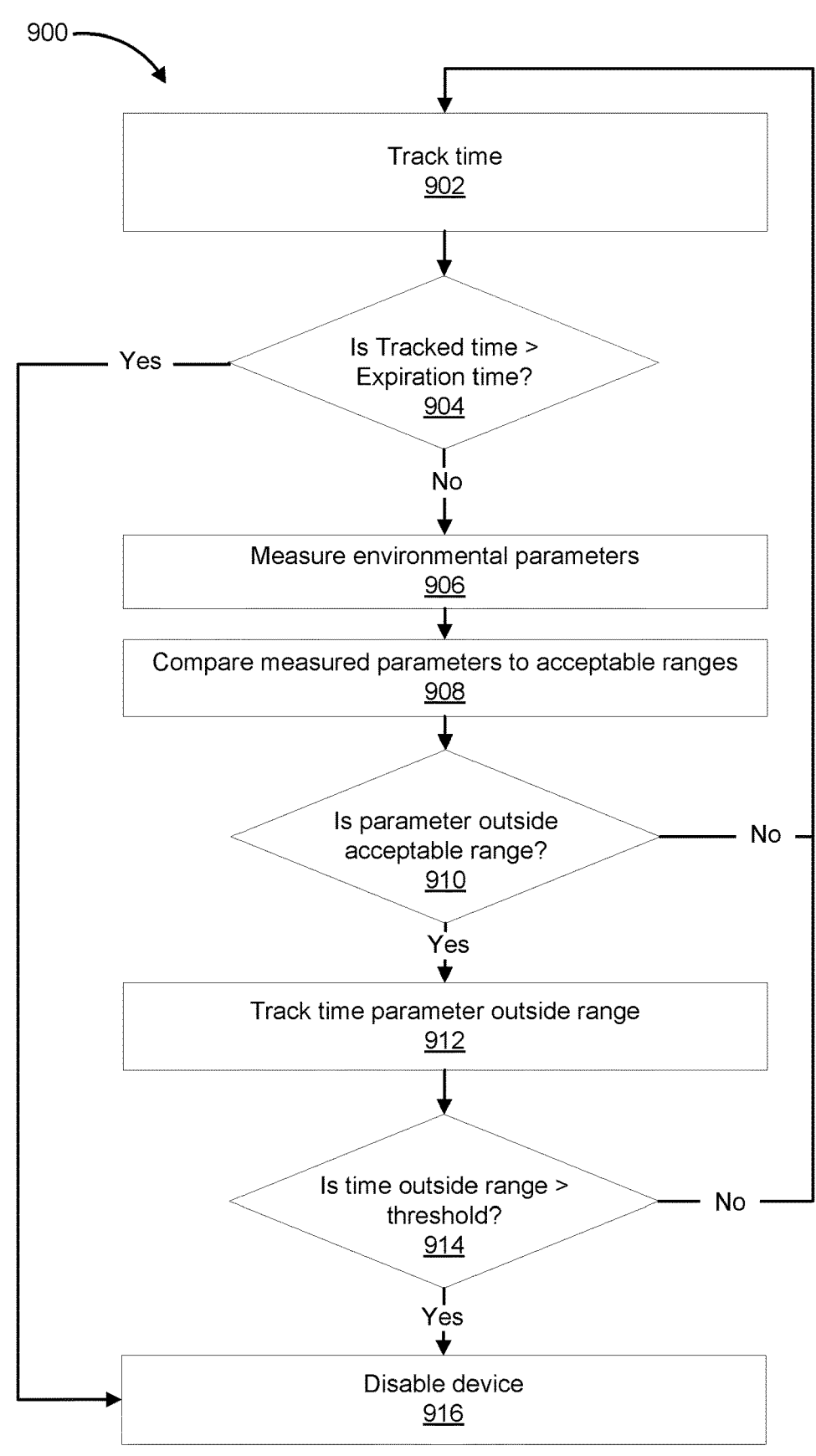
FIG. 9 is a flowchart illustrating another example process for tracking environmental conditions of a single-use diagnostics device from manufacture to use.

FIG. 9 is a flowchart illustrating another example process 900 for tracking environmental conditions of a single-use diagnostics device. Like the process 800, the process 900 is described with respect to the device 100 but may instead track the device 500 or another device.

The device 100 tracks 902 time after manufacturing, using an internal timer. The time from manufacture is periodically compared 904 to an expiration time limit and, if the time is exceeded, the device 100 can disable 916 the device. Periodically, the device 100 measures 906 environmental parameters such as temperature, humidity, and/or pressure. The device 100 can store the measured parameters in a memory. To save power, the device 100 may operate in a low power mode during shipment and storage, exiting the low power mode periodically to measure 906 the environmental parameters. For example, the device 100 may sample the environmental parameters at a frequency of approximately once every minute, or another frequency deemed appropriate.

The device 100 can compare 908 each sample of the environmental parameters to acceptable ranges. Acceptable ranges for temperature and humidity of the device 100 may be the ranges in which the reagents used in the device to analyze a biological sample are rated as stable. An acceptable range for pressure may be an expected pressure of a vacuum-sealed package.

If the device 100 determines 910 a measured environmental parameter is outside the respective acceptable range, the device 100 can track 912 an amount of time the parameter is outside the range. If the time exceeds a threshold time 914, the device 100 may be disabled 916. For example, while the acceptable temperature range of the device 100 may be 5° C. to 30° C., the device 100 may tolerate exposure to temperatures from 30° C. to 40° C. for short periods of time (e.g., less than 3 months) without risk of denaturation or damaging of the reagents. Thus, if the device 100 measures a temperature between 30° C. and 40° C., the device 100 can begin tracking 912 the time the temperature exceeds the acceptable range. If the temperature returns to less than 30° C. in less than the threshold time, the device 100 may not be disabled and may continue periodically measuring 906 the environmental parameters. Similarly, if the device 100 measures a pressure greater than an acceptable range, the device 100 may turn on an active mode to perform a diagnostic test and track 912 the amount of time since the pressure increase. If a biological sample is not added to the device 100 within a threshold amount of time, the device 100 may be disabled. The device 100 may use multiple different threshold times to determine whether to disable 916 the device, and different threshold times can be defined for different temperature and humidity ranges outside the acceptable ranges. For example, given an acceptable temperature range for the device 100 of 5° C. to 30° C., the device 100 may use a threshold time of 3 months for temperatures from 30° C. to 40° C., and a threshold time of 15 days from 40° C. to 50° C.

If the environmental parameters of the device 100 remain outside the acceptable ranges for longer than the threshold time, the device 100 can be disabled 914. As described above, disabling the device 100 can include executing program code to render the device 100 unusable, displaying a message or notification on the device 100, communicating a message to an external device, or otherwise communicating to a user that the device 100 should not be used.

The device 100 can recalculate an expiration time for the device based on how long an environmental parameter was outside the corresponding acceptable range. The device 100 may have a predefined expiration time, such as 365 days after manufacture, after which the reagents are presumed to have degraded below a desirable quality. The device 100 may expire at the predefined expiration time if the device 100 is not exposed to environmental conditions outside the acceptable ranges. If the device 100 determines an environmental parameter is outside an acceptable range, the device 100 can determine an expiration time that is less than the predefined expiration time. For example, the device 100 may expire a set length of time after being exposed to a high temperature or humidity, such as seven days after the exposure. A usable lifetime of the device 100 may be reduced by a fixed proportion after exposure to a high temperature or humidity. For example, the lifetime may be reduced to half of the time remaining between the exposure and the predetermined expiration time.

The expiration time calculated by the device 100 may depend on how far the detected temperature or humidity was from the acceptable ranges, how long the device 100 was exposed to environmental conditions outside the acceptable ranges, or whether multiple environmental conditions fell outside the acceptable ranges. For example, the total shelf life of a device 100 exposed to temperatures only below 30° C. may be 12 months, the total shelf life of a device 100 exposed to temperatures up to 35° C. may be 6 months, and the total shelf life of a device 100 exposed to temperatures up to 40° C. may be 3 months. The device 100 can calculate the expiration time by subtracting a time between manufacture and exposure to a temperature above 30° C. from the specified shelf life for the temperature. Similarly, the total shelf life of a device 100 exposed to relative humidities below 5% may be 12 months, the total shelf life of a device 100 exposed to relative humidities up to 10% may be 6 months, and the total shelf life of a device 100 exposed to relative humidities up to 15% may be 3 months. If a device 100 is exposed to both a temperature between 35-40° C. and a relative humidity between 10-15%, the total shelf life of the device 100 may be only one month. The device 100 can calculate the expiration time by subtracting a time between manufacture and exposure to a relative humidity above 5% from the specified shelf life for the humidity. The device 100 can display a notification when the predetermined or calculated expiration time has been reached, or can be disabled to prevent use.

In another implementation of detecting the environmental exposure from manufacture to use, in the case of some or all of the sensors being the type that permanently changes properties upon elevated environmental conditions, the environmental sensors 312, 314 and/or 320 may be measured only once or a few times by the microcontroller 316 before or during the use of the device 100.

Figure 10A:
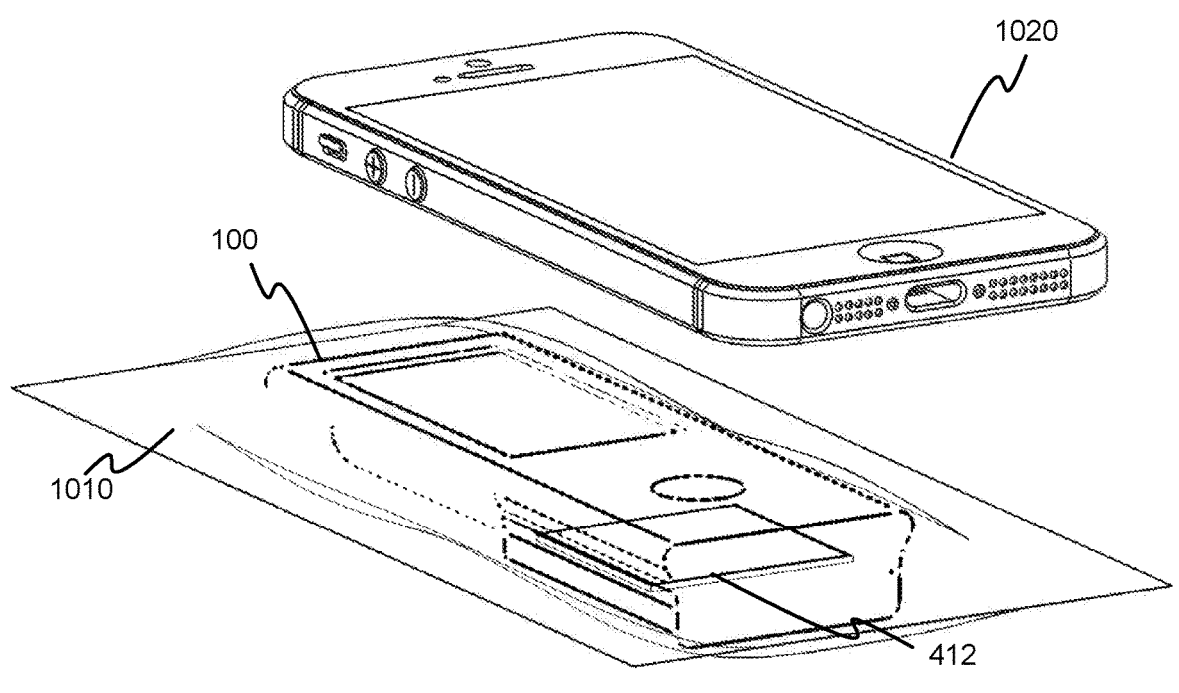
FIGS. 10A-10B illustrate example methods for communicating information about environmental parameters to a user before a diagnostics device is used.
Figure 10B:
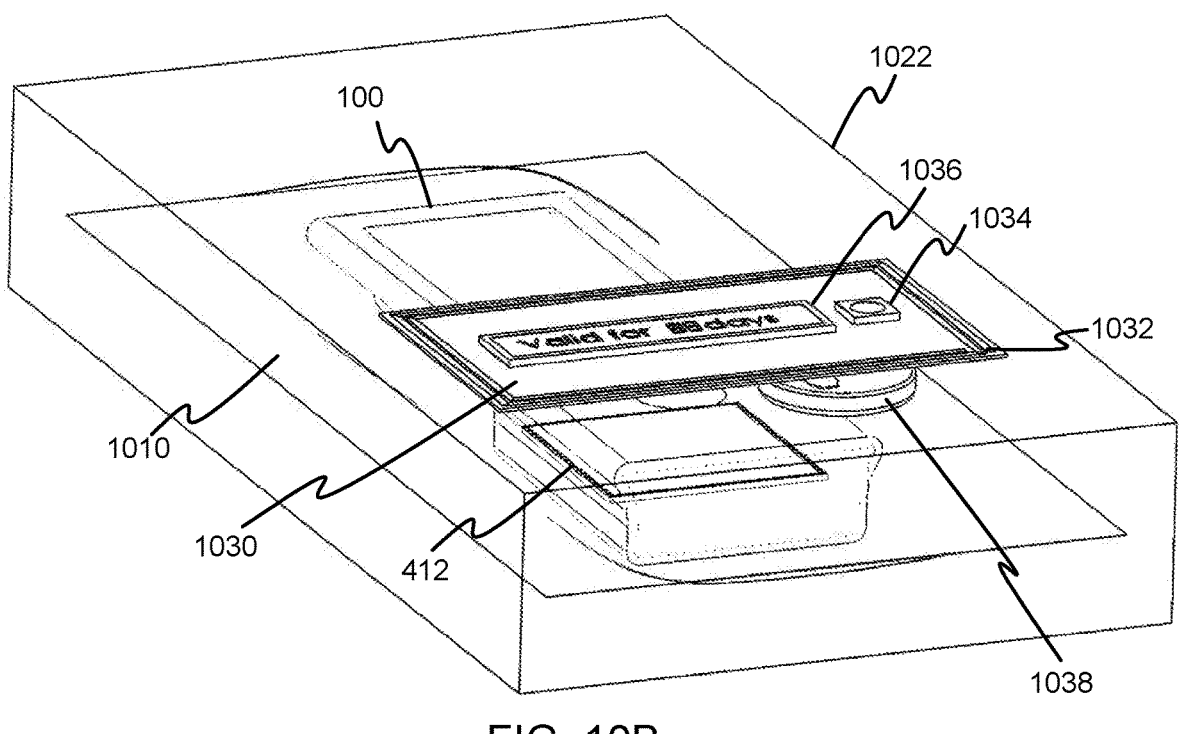

FIGS. 10A-10B illustrate examples of communicating information about environmental parameters to a user before the device 100 is used. In FIG. 10A, the device 100 can include an antenna 412 configured to wirelessly transmit data (e.g., via near field communication, RFID, or Bluetooth). The antenna 412 can be coupled to the microcontroller 316, and can transmit data describing environmental parameters experience by the device 100 to an external receiver. The device 100 can transmit some or all of the measurements of the environmental parameters, such as each sample of the temperature, humidity, and/or pressure or each sample that fell outside the acceptable ranges for the environmental parameters. The device 100 can transmit an assessment of quality of the device 100, such as a message indicating whether the environmental parameters have remained within their respective acceptable ranges or an estimation of time until the device 100 will expire. The device 100 can transmit a unique identifier of the device 100 via the antenna 412, associating the environmental parameter data with a unique device 100.

During shipment and storage, the device 100 can be enclosed in a package 1010 providing a barrier to humidity, dirt, or other conditions or substances that may damage the device 100. To check the quality of the device 100 without opening the package 1010, a user can use an external device 1020 with a wireless receiver, such as a mobile phone, to scan the device 100. The antenna 412 can transmit data to the external device 1020, where it may be evaluated by the user. The user may therefore scan a device 100 when the user intends to perform a diagnostic test and verify, at the time of use, whether the device 100 is suitable for use. A user may periodically scan devices 100 in storage to monitor storage conditions and quality of the devices 100. For example, hospital staff may periodically scan the devices 100 in storage to determine which devices 100 are still usable or to identify anomalous storage conditions. A dedicated wireless receiver, such as an RFID reader, can be stored with devices 100 to automatically read environmental parameter data at periodic intervals and upload the data to a database. For example, the data may be automatically uploaded to a hospital database, from which alerts can be generated when a particular device 100 is nearing its expiration date or is exposed to environmental conditions outside the acceptable ranges. By storing a history of environmental conditions experienced by a device 100, a hospital can use the particular environmental conditions when needed to verify the accuracy of a diagnostic test performed using the device 100.

FIG. 10B illustrates another example of communicating data from the device 100 to an external device. In the example of FIG. 10B, the device 100 and sealed pouch 1010 can be enclosed in a shipping box 1022. A package display 1030 can be provided on the outside of the shipping box 1022. The package display can include an antenna 1032 configured to receive data transmitted by the antenna 412 in the device 100. The antenna 1032 can be activated to retrieve the data from the device 100 when a user presses a read activation button 1034, or can be controlled by a microcontroller that periodically activates the antenna 1032. Data retrieved from the device 100 can be displayed on an electronic display 1036. As shown in FIG. 10B, the display 1036 can provide information about the quality of the device 100, such as a number of days until the device 100 will expire. The display 1036 can provide information to a user in other manners. For example, the display 1036 can be an LED that, when illuminated, indicates to a user that the device 100 has been exposed to environmental conditions outside the acceptable range and should not be used. A battery 1038 in the package display 1030 can provide power to the display 1036, antenna 1032, read activation button 1034, and/or microcontroller.

Each of the individual variations described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations that may become obvious to those skilled in the art in view of this disclosure.

The invention claimed is:

1. A self-contained single-use electronic diagnostic device for detecting analytes in biological fluids, comprising:

a sample inlet area;

a fluidic structure;

a fill sensor for detecting a first volume amount of the sample, wherein the device is configured so that the device exits a lower power mode and enters a higher power active mode when the first volume amount is detected, and wherein the device is configured to be disabled if the sample is not added to the device within a threshold amount of time after the device enters an active state;

an inlet cover configured to cover and uncover the sample inlet area, and wherein the device is configured to activate processing of the sample when the inlet cover covers the inlet area;

a sample reaction area with one or more detection areas comprising dried or lyophilized reagents;

a circuit board comprising:

a single LED light source configured to illuminate the one or more detection areas; and one or more optical detectors positioned to receive light reflected from the one or more detection areas, thereby enabling the device to detect one or more analytes;

a battery for providing power to the device;

a temperature sensor for measuring temperature;

a vacuum package configured to provide a barrier to humidity;

a pressure sensor and/or pressure switch, wherein the pressure sensor and/or pressure switch are configured to detect if the package is opened;

a microcontroller in data communication with the temperature sensor, and wherein the microcontroller is configured to compare the temperature measured by the temperature sensor with at least one temperature limit;

wherein the temperature sensor and microcontroller are configured to monitor the temperature from a time of manufacturing of the device until a time of end-use of the device, and wherein the microcontroller is configured to render the device unusable if the microcontroller determines that the measured temperature crosses the temperature limit;

wherein the device is configured to operate in the lower power mode during shipment and storage except to exit the lower power mode periodically to measure one or more environmental parameters; and a near field communication circuit for communicating a quality assessment of the device with an external device.

2. The device of claim 1, wherein the microcontroller is configured to reduce a frequency at which the temperature sensor measures the temperature to save power.

3. A system comprising the device of claim 1, wherein the microcontroller is configured to render the device unusable if the microcontroller determines that the package has been opened too long before end-use.

4. The system of claim 3, wherein the microcontroller is configured to reduce a frequency at which the pressure sensor and/or pressure switch measure a pressure in the package to save power.

5. The system of claim 3, wherein the pressure sensor or pressure switch is used to detect the opening of the packaging and thereby activating the measurement process in the device.

6. The device of claim 1, further comprising a non-volatile memory, and wherein the memory is configured to store calibration factors.

7. The device of claim 1, further comprising an LCD display configured to display measurement results to a user.

8. The device of claim 1, further comprising a non-volatile memory, and wherein the results can be stored in the memory.

9. The device of claim 1, the near field communication circuit further comprising an antenna configured to transmit the results to a remote system.

10. The device of claim 1, further comprising an optical and/or infra-red wireless transmitter configured to transmit the results to a remote system.

11. The device of claim 1, further comprising an electrical connector configured to transmit the results to a remote system.

12. The device of claim 1, wherein multiple processing steps are controlled by use of spring elements and a resistive elements that are connected to electrical conducting elements by use of meltable material that is solid at room temperature but that melts below the destructive temperature of the other components in connection with the meltable material and where the heating of the resistive element will lead to the melting of the meltable material and whereby mechanical links will be broken and whereby the breaking of the mechanical links will lead to the springs activating several fluid movements at different time points during the reaction.

13. The device of claim 1, wherein the device detects DNA or RNA target fragments corresponding to a genomic sequence.

14. The device of claim 13, wherein the device is configured to perform a sample preparation comprising lysing and filtering of the sample prior to detection of DNA or RNA target fragments.

15. The device of claim 1 where the microcontroller has a low power standby mode of less than 10uA.

16. The device of claim 1 where the device can track the time that one or more environmental parameters are outside a respective range; where the device will be disabled if a time limit has been exceeded for an environmental parameter outside a range.

17. The device of claim 1 where the device has different threshold times for multiple different environmental ranges outside an acceptable range such that the device will be disabled upon exceeding an environmental parameter range for a certain amount of time depending on a deviation from the acceptable environmental parameter range.

18. The device of claim 1, the near field communication circuit further comprising an antenna configured to transmit the results to a remote system using Near Field Communication or RFID or Bluetooth communication.

19. The device of claim 1, further comprising a temperature-controlled chamber for isothermal nucleic acid detection using fluorescence detection.

20. The device of claim 1, wherein the reagents comprise an enzyme configured to optically change upon an excessive change of temperature and/or humidity.

21. The device of claim 1, wherein the one or more environmental parameters comprise time and temperature.

22. The device of claim 1, the near field communication circuit further comprising an antenna configured for near field wireless communication, wherein the device is configured to transmit a unique identifier of the device via the antenna, and wherein the circuit board further comprises the microcontroller, and the temperature sensor.

23. A self-contained electronic diagnostic device for detecting analytes in biological fluids, comprising:

a sample inlet area;

a fluidic structure;

a fill sensor for detecting a first volume amount of the sample, wherein the device is configured so that the device exits a lower power mode and enters a higher power active mode when the first volume amount is detected, and wherein the device is configured to be disabled if the sample is not added to the device within a threshold amount of time after the device enters an active state;

an inlet cover configured to cover and uncover the sample inlet area, and wherein the device is configured to activate processing of the sample when the inlet cover covers the inlet area;

a sample reaction area with one or more detection areas comprising dried reagents;

a circuit board comprising:

a single LED light source for illuminating the one or more detection areas; and one or more optical detectors positioned to receive light reflected from the one or more detection areas, thereby enabling the device to detect one or more analytes;

a battery for providing power to the device;

a temperature sensor for measuring temperature;

a humidity sensor;

a microcontroller in data communication with the temperature sensor and humidity sensor, and wherein the microcontroller is configured to compare the temperature measured by the temperature sensor with at least one temperature limit and wherein the microcontroller is configured to compare the humidity measured by the humidity sensor with at least one humidity limit;

wherein the temperature sensor and the humidity sensor and microcontroller are configured to monitor the temperature and humidity from a time of manufacturing of the device until a time of end-use of the device, and wherein the microcontroller is configured to render the device unusable if the microcontroller determines that the measured temperature crosses the temperature limit or the measured humidity crosses the humidity limit;

wherein the device is configured to operate in the lower power mode during shipment and storage except to exit the lower power mode periodically to measure one or more environmental parameters; and a near field communication circuit for communicating a quality assessment of the device with an external device.

24. The device of claim 23, wherein the humidity sensor is only measured at certain intervals, so as to save power.

25. The device of claim 23, further comprising a time tracker for tracking elapsed time from manufacturing of the device until end-use of the device; and wherein the microcontroller is configured to render the device unusable if the elapsed time exceeds an expiration time.

26. The device of claim 23, further comprising a non-volatile memory, and wherein the memory is configured to store calibration factors.

27. The device of claim 23, further comprising an LCD display configured to display measurement results to a user.

28. The device of claim 23, further comprising a non-volatile memory, and wherein the results can be stored in the memory.

29. The device of claim 23, further comprising an optical and/or infra-red wireless transmitter configured to transmit the results to a remote system.

30. The device of claim 23, further comprising an electrical connector configured to transmit the results to a remote system.

31. The device of claim 23, wherein multiple processing steps are controlled by use of a spring elements and a resistive elements that are connected to electrical conducting elements by use of meltable material that is solid at room temperature but that melts below the destructive temperature of the other components in connection with the meltable material and where the heating of the resistive element will lead to the melting of the meltable material and whereby mechanical links will be broken and whereby the breaking of the mechanical links will lead to the springs activating several fluid movements at different time points during the reaction.

32. The device of claim 23, wherein the device detects DNA or RNA target fragments corresponding to a genomic sequence.

33. The device of claim 32, wherein the device is configured to perform a sample preparation comprising lysing and filtering of the sample prior to detection of DNA or RNA target fragments.

34. The device of claim 23 where the microcontroller has a low power standby mode of less than 10 uA.

35. The device of claim 23 where the device can track the time that one or more environmental parameters are outside a respective range; where the device will be disabled if a time limit has been exceeded for an environmental parameter outside a range.

36. The device of claim 23 where the device has different threshold times for multiple different environmental ranges outside an acceptable range such that the device will be disabled upon exceeding an environmental parameter range for a certain amount of time depending on a deviation from the acceptable environmental parameter range.

37. The device of claim 23, the near field communication circuit further comprising an antenna configured to transmit the results to a remote system using Near Field Communication or RFID or Bluetooth communication.

38. The device of claim 23, wherein the reagents comprise an enzyme configured to optically change upon an excessive change of temperature and/or humidity.

39. The device of claim 23, wherein the one or more environmental parameters comprise time and temperature.

40. The device of claim 23, the near field communication circuit further comprising an antenna configured for near field wireless communication, wherein the device is configured to transmit a unique identifier of the device via the antenna, and wherein the circuit board further comprises the microcontroller, and the temperature sensor.

41. A self-contained electronic diagnostic device for detecting analytes in biological fluids, comprising:

a sample inlet area;

a fluidic structure;

a fill sensor for detecting a first volume amount of the sample, wherein the device is configured so that the device exits a lower power mode and enters a higher power active mode when the first volume amount is detected, and wherein the device is configured to be disabled if the sample is not added to the device within a threshold amount of time after the device enters an active state;

an inlet cover configured to cover and uncover the sample inlet area, and wherein the device is configured to activate processing of the sample when the inlet cover covers the inlet area;

a sample reaction area with one or more detection areas comprising dried or lyophilized reagents;

a circuit board comprising:

a single LED light source for illuminating the one or more detection areas; and one or more optical detectors positioned to receive light reflected from the one or more detection areas, thereby enabling the device to detect one or more analytes;

a battery for providing power to the device;

a temperature sensor for measuring temperature;

a humidity sensor;

a microcontroller in data communication with the temperature sensor and humidity sensor, and wherein the microcontroller has a time function, and wherein the microcontroller is configured to compare the temperature measured by the temperature sensor with at least two temperature limits, and where the microcontroller is configured to render the device unusable if the device has exceeded a first temperature limit for a first period of time and where the microcontroller is configured to render the device unusable if the device has exceeded a second temperature limit for a second period of time, thereby having a longer shelf life at lower temperatures;

and wherein the microcontroller is configured to compare the humidity measured by the humidity sensor with at least two humidity limit, and where the microcontroller is configured to render the device unusable if the device has exceeded a first humidity limit for a first period of time and where the microcontroller is configured to render the device unusable if the device has exceeded a second humidity limit for a second period of time, thereby having a longer shelf life at lower humidities;

wherein the device is configured to operate in the lower power mode during shipment and storage except to exit the lower power mode periodically to measure one or more environmental parameters; and a near field communication circuit for communicating a quality assessment of the device with an external device.

42. The device of claim 41, wherein the device detects DNA or RNA target fragments corresponding to a genomic sequence, and wherein the device is configured to perform a sample preparation comprising lysing and filtering of the sample prior to detection of DNA or RNA target fragments.

\* \* \* \* \*